United States Patent
Jugl et al.

(10) Patent No.: US 10,314,978 B2
(45) Date of Patent: Jun. 11, 2019

(54) ASSEMBLY FOR A DRUG DELIVERY DEVICE

(71) Applicant: SANOFI-AVENTIS DEUTSCHLAND GMBH, Frankfurt am Main (DE)

(72) Inventors: Michael Jugl, Frankfurt am Main (DE); Axel Teucher, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 690 days.

(21) Appl. No.: 14/763,870

(22) PCT Filed: Feb. 3, 2014

(86) PCT No.: PCT/EP2014/051978
§ 371 (c)(1),
(2) Date: Jul. 28, 2015

(87) PCT Pub. No.: WO2014/118357
PCT Pub. Date: Aug. 7, 2014

(65) Prior Publication Data
US 2015/0359970 A1 Dec. 17, 2015

(30) Foreign Application Priority Data
Feb. 4, 2013 (EP) .................................. 13153796

(51) Int. Cl.
*A61M 5/315* (2006.01)
*A61M 5/50* (2006.01)

(52) U.S. Cl.
CPC .... *A61M 5/31541* (2013.01); *A61M 5/31501* (2013.01); *A61M 5/31528* (2013.01);
(Continued)

(58) Field of Classification Search
CPC ...... A61M 2005/3154; A61M 5/31528; A61M 5/31501; A61M 5/31585; A61M 5/502
See application file for complete search history.

(56) References Cited

U.S. PATENT DOCUMENTS

2008/0154211 A1\* 6/2008 Moller .............. A61M 5/31536
604/211
2009/0240195 A1\* 9/2009 Schrul ................ A61M 5/2448
604/71
(Continued)

FOREIGN PATENT DOCUMENTS

EP 0307367 3/1989
WO WO-2006089767 A1 \* 8/2006 ........ A61M 5/31536
(Continued)

OTHER PUBLICATIONS

European Search Report for EP App. No. 13153796.1, dated May 27, 2013.
(Continued)

*Primary Examiner* — Jenna Zhang
(74) *Attorney, Agent, or Firm* — Fish & Richardson P.C.

(57) ABSTRACT

An assembly for a drug delivery device is provided, wherein the assembly comprises an actuator which is configured to perform a setting movement in order to set a dose and which is configured to perform a dispense movement in order to dispense a dose and a piston rod which is configured to be moved in a distal direction in order to dispense a dose, and a snap feature which is configured to snap into engagement with the piston rod. The snap feature may be configured to inhibit a dispense movement of the actuator and/or a setting movement of the actuator when a maximum amount of medication has been delivered.

14 Claims, 3 Drawing Sheets

(52) U.S. Cl.
CPC ........ *A61M 5/31585* (2013.01); *A61M 5/502* (2013.01); *A61M 2005/3154* (2013.01)

(56) References Cited

U.S. PATENT DOCUMENTS

| | | | | |
|---|---|---|---|---|
| 2010/0036320 | A1* | 2/2010 | Cox | A61M 5/24 604/135 |
| 2010/0087799 | A1* | 4/2010 | Galbraith | A61M 5/2448 604/518 |
| 2010/0274198 | A1* | 10/2010 | Bechtold | A61M 5/31551 604/189 |
| 2010/0324527 | A1* | 12/2010 | Plumptre | A61M 5/31536 604/500 |
| 2011/0004191 | A1* | 1/2011 | Jones | A61M 5/31538 604/506 |
| 2012/0143146 | A1* | 6/2012 | Strehl | A61M 5/24 604/208 |
| 2013/0079725 | A1* | 3/2013 | Shang | A61M 5/20 604/189 |
| 2014/0194830 | A1* | 7/2014 | Nzike | A61M 5/31541 604/211 |
| 2014/0207073 | A1* | 7/2014 | Shang | A61M 5/2033 604/189 |

FOREIGN PATENT DOCUMENTS

| | | | | |
|---|---|---|---|---|
| WO | 2008/058665 | | 5/2008 | |
| WO | WO-2010139691 | A1 * | 12/2010 | .............. A61M 5/24 |
| WO | 2012/017036 | | 2/2012 | |
| WO | WO 2012017036 | A1 * | 2/2012 | ........ A61M 5/31541 |
| WO | WO-2012017036 | A1 * | 2/2012 | ........ A61M 5/31541 |

OTHER PUBLICATIONS

International Search Report and Written Opinion for Int. App. No. PCT/EP2014/051978, dated Apr. 22, 2014.
International Preliminary Report on Patentability in International Application No. PCT/EP2014/051978, dated Aug. 4, 2015, 8 pages.

* cited by examiner

ASSEMBLY FOR A DRUG DELIVERY DEVICE

CROSS REFERENCE TO RELATED APPLICATIONS

The present application is a U.S. National Phase Application pursuant to 35 U.S.C. § 371 of International Application No. PCT/EP2014/051978 filed Feb. 3, 2014, which claims priority to European Patent Application No. 13153796.1 filed Feb. 4, 2013. The entire disclosure contents of these applications are herewith incorporated by reference into the present application.

TECHNICAL FIELD

The present disclosure relates to an assembly for a drug delivery device.

BACKGROUND

A drug delivery device and an assembly for a drug delivery device are described for example in document WO 2008/058665 A1.

SUMMARY

It is an object of the present invention to provide an assembly for a drug delivery device having improved properties.

An assembly for a drug delivery device is provided, wherein the assembly comprises an actuator which is configured to perform a setting movement in order to set a dose and which is configured to perform a dispense movement in order to dispense a dose. The assembly further comprises a piston rod which is configured to be moved in a distal direction in order to dispense a dose, and a snap feature which is configured to snap into engagement with the piston rod. The snap feature may be configured to inhibit a dispense movement of the actuator and/or a setting movement of the actuator. In particular, a setting movement and/or a dispense movement may be inhibited when a maximum amount of medication has been delivered. The maximum amount of medication may be for example the amount of medication available in a cartridge.

An advantage of a snap feature which is configured to snap into engagement with the piston rod is that the snap feature may permanently lock the assembly. When the assembly is locked, a movement of any component of the assembly may be inhibited.

According to one embodiment, the snap feature is configured as a resilient member. In particular, the snap feature may comprise the shape of a ring. The snap feature may be arranged concentrically around the piston rod. In particular, the snap feature may be in contact with the piston rod throughout the use of the drug delivery device, i.e. also when it is not engaged with the piston rod. In particular, the snap feature may comprise at least one protrusion which may be in contact with the piston rod. The at least one protrusion may be arranged at an inner surface of the snap feature. For example, the snap feature may comprise two protrusions, which may be oppositely arranged.

According to one embodiment, the snap feature is preloaded due to an interaction with the piston rod. In particular, the snap feature may be deflected in a radial outward direction due to the presence of the piston rod when the snap feature is not engaged with the piston rod.

According to one embodiment, the snap feature is preloaded before snapping into engagement with the piston rod. In particular, the snap feature may be preloaded throughout the use of the drug delivery device. When snapping into engagement with the piston rod, the snap feature may be enabled to relax. In particular, the snap feature may deflect in a radial inward direction, thereby engaging with the piston rod. In particular, the at least one protrusion of the snap feature may engage with the piston rod. When the snap feature is in engagement with the piston rod, the snap feature may still be slightly preloaded or it may be in an undeflected state.

According to one embodiment the snap feature is configured to inhibit a dispense movement of the actuator after a last setting movement when a maximum amount of medication has been delivered. According to a further embodiment, the snap feature is configured to inhibit a setting movement of the actuator after a last dispense movement when a maximum amount of medication has been delivered.

The setting movement of the actuator may be a translational movement in a proximal direction. For example, the setting movement may be an axial, non-rotational movement. Alternatively, the setting movement may be a combined axial and rotational movement. Alternatively, the setting movement may be a purely rotational movement. The dispense movement of the actuator may be a movement in a distal direction, for example a purely axial movement. In particular, the actuator may be pushed in a distal direction by a user in order to dispense a dose. The actuator may be configured as a button.

The term "proximal direction" may describe a direction away from a dispensing end of the device. Analogously, the proximal end may be an end which is furthest away from a dispensing end. The term "distal direction" may describe a direction towards a dispensing end of the device.

According to one embodiment, the snap feature is configured to snap into engagement with the piston rod after a last setting movement of the actuator. Alternatively, the snap feature may be configured to snap into engagement with the piston rod after a last dispense movement.

According to one embodiment, the piston rod comprises at least one recess, wherein the snap feature is configured to engage with the recess. The at least one recess of the piston rod may be configured as a hole. The recess may extend in a direction which is perpendicular to a longitudinal axis of the device. According to one embodiment, the recess may extend through the piston rod. As an example, the piston rod may comprise two recesses, which may be oppositely arranged. The snap feature may be configured such that the at least one protrusion of the snap feature may engage into the at least one recess of the piston rod, in particular after a last setting or a last dispense movement of the actuator.

According to one embodiment, the snap feature is configured to produce an audible click when snapping into engagement with the piston rod. The audible click may indicate to a user that a maximum amount of medication has been delivered. Alternatively, the audible click may indicate to a user that a last dose is ready to be delivered.

According to one embodiment, the assembly comprises a drive member which is configured to drive the piston rod towards a distal end of the device in order to deliver a dose of medication. The drive member may be configured as a drive sleeve. The drive member may be arranged concentrically around the piston rod. In particular, the drive member may be coupled with the piston rod, for example by means of a thread. The drive member may comprise at least one recess, wherein the snap feature is permanently engaged with the at least one recess of the drive member. In particular, the at least one protrusion of the snap feature may be permanently engaged with the at least one recess of the drive member. The at least one recess may be configured as a hole. The at least one recess may extend through the drive member in a radial direction towards a longitudinal axis of the device. For example, the drive member may comprise two recesses, which may be oppositely arranged. According to one embodiment, the snap feature is arranged concentrically around the drive member.

According to one embodiment, the snap feature is rotationally and axially fixed with respect to the drive member. In particular, the snap feature may be fixed with respect to the drive member by means of the at least one protrusion of the snap feature being engaged with the at least one recess of the drive member.

The drive member may be fixedly coupled to the actuator. For example, the drive member and the actuator are manufactured as one part. In particular, a movement of the actuator may cause a movement of the drive member. Since the drive member and the actuator may be fixedly coupled to each other, the movement of the drive member may correspond to the movement of the actuator.

During the setting of a dose, the drive member may be moved relative to the piston rod. In particular, the drive member may be moved along the piston rod in a proximal direction. For example, the drive member may perform an axial, non-rotational movement during the setting of a dose. Alternatively, the drive member may perform a combined axial and rotational movement. In particular, the drive member may be rotated along the piston rod. Alternatively the drive member may perform a purely rotational movement with respect to the piston rod. When the snap feature has engaged the piston rod, a relative movement between the drive member and the piston rod may be inhibited. Thereby, a further setting movement may be inhibited.

According to an embodiment, a further dispense movement may be inhibited when the snap feature has engaged with the piston rod. In particular, a further dispense movement may be inhibited by the snap feature in case that the drive member and the piston rod are configured to be moved relative to each other during the dispense movement Alternatively, a further dispense movement may be enabled when the snap feature has engaged with the piston rod. In particular, a further dispense movement may be enabled when the snap feature has engaged with the piston rod in case that the drive member and the piston rod are configured to be fixed with respect to each other during a dispense movement. After the last dispense movement, a further setting movement may be inhibited by the snap feature. For example, the snap feature may snap into engagement with the piston rod when the drive member is in a most proximal position with respect to the piston rod. For example, the snap feature may snap into engagement with the piston rod at the end of a setting movement.

During the dispensing of a dose, the piston rod and the drive member may be fixed with respect to each other. In particular, there may be no relative movement between the piston rod and the drive member. In particular, the piston rod and the drive member may be moved together in a distal direction. In an alternative embodiment, the piston rod and the drive member may move relative to each other during the dispense operation. In particular, the piston rod may rotate and axially move with respect to the drive member during the dispensing of a dose. In particular, a further dispense movement may be inhibited when the snap feature has engaged with the piston rod. Alternatively, a further dispense movement may be enabled when the snap feature has engaged with the piston rod.

According to one embodiment, the drive member and the piston rod are locked with respect to each other when the snap feature is engaged with the piston rod. When the drive member and the piston rod are locked with respect to each other, any relative movement between the drive member and the piston rod is inhibited.

The snap feature may snap into engagement with the piston rod when the piston rod and the drive member are in a predetermined position with respect to each other. In particular, the snap feature may be engaged with the piston rod when the at least one recess of the drive member is aligned with the at least one recess of the piston rod. In this state, the snap feature may be enabled to relax. In particular, the snap feature may be enabled to deflect in a radial inward direction. In particular, the at least one protrusion of the snap feature may further move through the at least one recess of the drive member and engage the at least one recess of the piston rod.

According to one embodiment, a last setting movement is enabled and a dispense movement is inhibited, after the snap feature has engaged with the piston rod. Alternatively, a last dispense movement is enabled and a further setting movement is inhibited after the snap feature has engaged with the piston rod. Alternatively, a setting movement and a dispense movement are inhibited after the snap feature has engaged with the piston rod.

For example, when the snap feature has engaged with the piston rod after a last setting movement, a relative movement between the drive member and the piston rod may be inhibited. Thereby, a movement in a distal direction of the drive member and the piston rod may be inhibited in the case that a dispense operation requires a relative movement of the drive member and the piston rod. Thereby, the device may be locked. In particular, no further setting or dispense movement may be possible. In this state, the actuator may protrude from a housing of the assembly. Thereby, an indication may be given to a user that the device is empty.

According to a further example, when the snap feature has engaged with the piston rod after a last setting movement, a distal movement of the drive member and the piston rod may be enabled. In particular, a distal movement of the drive member and the piston rod may be enabled in the case that a dispense operation does not involve a relative movement between the drive member and the piston rod. In particular, an axial, non-rotational movement of the drive member and the piston rod may be enabled. Thereby, a last dose may be delivered. A further setting movement may be inhibited after the dispensing of the last dose, since the drive member may not be rotated along the piston rod in a proximal direction.

According to a further embodiment, the snap feature may engage with the piston rod after a last dispense movement. In particular, the snap feature may engage with the piston rod in the case that the drive member and the piston rod are moved relative to each other during the dispensing of a dose. For example, the piston rod may be moved in a proximal direction with respect to the drive member. In particular, the piston rod may rotate and axially move in a proximal direction with respect to the drive member. Due to the snap feature engaging with the piston rod, the assembly may be locked after a dispense movement. In particular, a further setting movement and a further dispense movement may be inhibited.

Furthermore, a drug delivery device is provided, the drug delivery device comprising an assembly which is configured as previously described. In particular, the drug delivery device may comprise a snap feature which is configured to snap into engagement with the piston rod, wherein the snap feature is configured to inhibit a dispense movement of the actuator and/or a setting movement after a last dispense movement when a maximum amount of medication has been delivered.

The drug delivery device may be an injection device. The drug delivery device may be a pen-type device. The drug delivery device may be a fixed dose device such that the amount of medication which is delivered during one dispense operation is predetermined. In particular, a user may not be enabled to vary the size of the dose. Alternatively, the drug delivery device may be a variable dose device, such that the amount of medication which is delivered during one dispense operation may be selected by a user. The drug delivery device may be configured for multiple dose applications. The medication may be delivered to a user by means of a needle. The device may be delivered to a user in a fully assembled condition ready for use. The drug delivery device may be a disposable device. The term "disposable" means that the drug delivery device cannot be reused after an available amount of medication has been delivered from the drug delivery device. The drug delivery device may be configured to deliver a liquid medication. The medication may be, for example, insulin.

The term "medication", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-er-   Ser-Gly-Ala-Pro-Pro-Pro-Ser-NH2.

Exendin-4 derivatives are for example selected from the following list of compounds:

-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4 (1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4 (1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4 (1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Further features, refinements and expediencies become apparent from the following description of the exemplary embodiments in connection with the figures.

DETAILED DESCRIPTION

Figure 1:
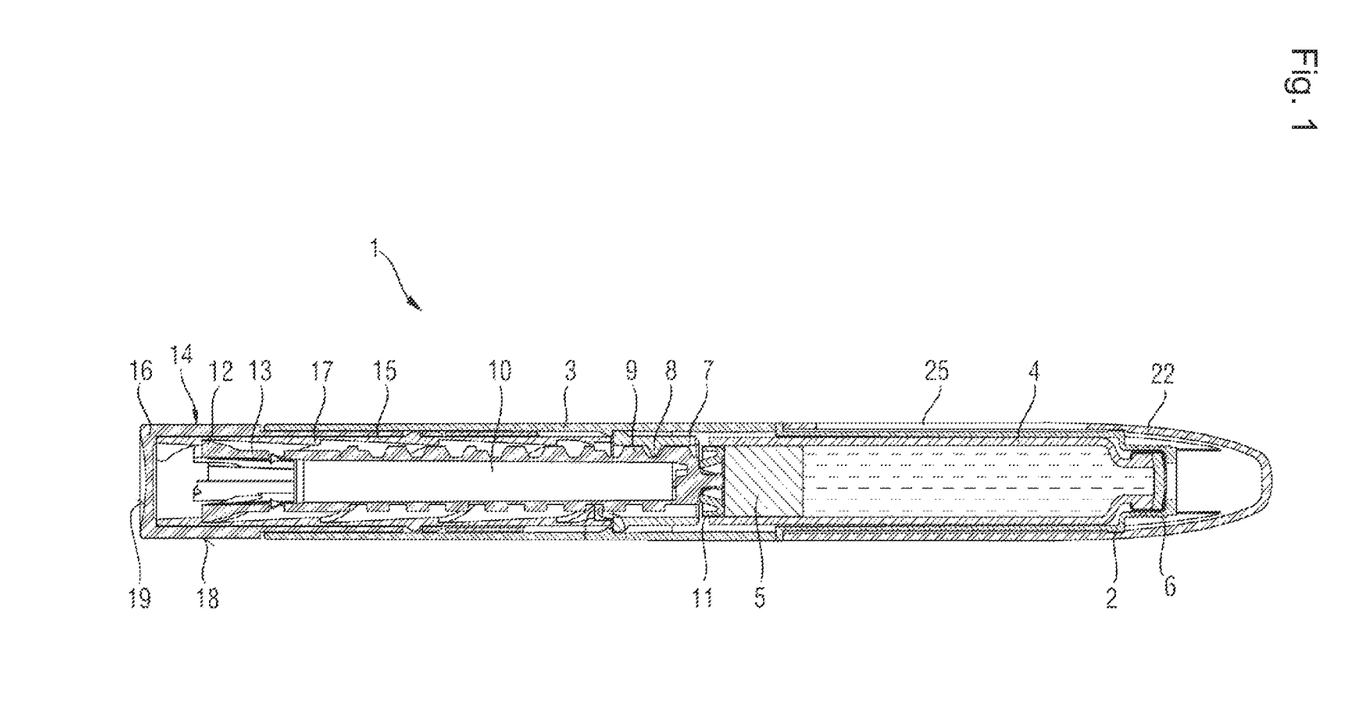
FIG. 1 shows a drug delivery device in a sectional view.

FIG. 1 shows a sectional view of a drug delivery device 1. The drug delivery device 1 comprises a cartridge retaining part 2, and a main housing part 3. The proximal end of the cartridge retaining part 2 and the distal end of the main housing 3 are secured together by any suitable means known to the person skilled in the art. In the illustrated embodiment, the cartridge retaining part 2 is secured within the distal end of the main housing part 3.

A cartridge 4 from which a number of doses of a medicinal product may be dispensed is provided in the cartridge retaining part 2. A piston 5 is retained in the proximal end of the cartridge 4.

A removable cap 22 is releasably retained over the distal end of the cartridge retaining part 2. The removable cap 22 is optionally provided with one or more window apertures through which the position of the piston 5 within the cartridge 4 can be viewed.

The distal end of the cartridge retaining part 2 in the illustrated embodiment, is provided with a distal threaded region 6 designed for the attachment of a suitable needle assembly (not shown) to enable medicament to be dispensed from the cartridge 4.

In the illustrated embodiment, the main housing part 3 is provided with an internal housing 7. The internal housing 7 is secured against rotational and/or axial movement with respect to the main housing part 3. The internal housing 7 is provided with a threaded circular opening 8 extending through the distal end of the internal housing 7. In the illustrated embodiment the threaded circular opening 8 comprises a series of part threads rather than a complete thread. Alternatively, the internal housing 7 may be formed integrally with the main housing part 3. Additionally, the internal housing 7 is provided with a plurality of guide slots and pawl means.

A first thread 9 is formed at the distal end of the piston rod 10. The piston rod 10 is of generally circular cross-section. The first thread 9 of the piston rod 10 extends through and is threadedly engaged with the threaded circular opening 8 of the internal housing 7. A pressure foot 11 is located at the distal end of the piston rod 10. The pressure foot 11 is disposed to abut the proximal face of the piston 5. A second thread 12 is formed at the proximal end of the piston rod 10. In the illustrated embodiment the second thread 12 comprises a series of part threads, rather than a complete thread, formed on flexible arms 13 of the piston rod 10.

The first thread 9 and the second thread 12 are oppositely disposed.

In the illustrated embodiment the first thread 9 is provided with a plurality of features (not shown) that cooperate with the part threads of the threaded circular opening 8 to prevent movement of the piston rod 10 in the proximal direction during setting of the dose.

A drive member 14 extends about the piston rod 10. The drive member 14 is configured as a drive sleeve. The drive member 14 comprises a threaded part 15 of a generally cylindrical cross-section. An actuator 16 is located at a proximal end of the drive member 14. The threaded part 15 and the actuator 16 are secured to each other to prevent rotational and/or axial movement there between. Alternatively, the drive member 14 may be a unitary component consisting of an integrated threaded part 15 and actuator 16.

In the illustrated embodiment, the threaded part 15 is provided with a longitudinally extending helical thread 17 formed on the internal cylindrical surface. The flank of the proximal side of the helical thread 17 is designed to maintain contact with the second thread 12 of the piston rod 10 when dispensing a dose, whilst the flank of the distal side of the helical thread 17 is designed to allow the second thread 12 of the piston rod 10 to disengage when setting a dose. In this way the helical thread 17 of the threaded part 15 is releasably engaged with the second thread 12 of the piston rod 10.

The drive member 14 has a plurality of features formed on the external surface designed to move axially within the guide slots of the internal housing 7. These guide slots define the extent of permissible axial movement of the drive member 14 with respect to the housing part 3. In the illustrated embodiment the guide slots also prevent rotational movement of the drive member 14 relative to the main housing part 3.

The actuator 16 has a plurality of grip surfaces 18 and a dispensing face 19.

To increase intuitiveness of the operation of the device, the main housing part 3 may be provided with a window aperture through which graphical status indicators, provided on the drive member 14, can be viewed.

Operation of the drug delivery device in accordance with the present invention will now be described.

To set a dose a user grips the grip surfaces 18 of the drive member 14. The user then pulls the drive member 14 in a proximal direction away from the main housing part 3.

The piston rod 10 is prevented from moving proximally by the part threads of the threaded circular opening 8 of the internal housing 7 interacting with thread features on the first thread 9 of the piston rod 10 or by any other suitable means. As the drive member 14 travels in the proximal direction relative to the piston rod 10, the second thread 12 of the piston rod 10 is displaced radially inwards by the flank of the distal side of helical thread 17 of the drive member 14.

The proximal travel of the drive member 14 is limited by the guide slots (not shown) of the internal housing 7 a distance corresponding to essentially one thread pitch of the helical thread 17 of the drive member 14. At the end of the travel of the drive member 14, the second thread 12 of the piston rod 10 engages with the helical thread 17 under the action of the flexible arms 13 of the piston rod 10. By this action the drive member 14 is displaced a distance essentially equal to one pitch of the helical thread 17 of the drive member 14 in the proximal direction relative to the piston rod 10. The action of the second thread 12 positively engaging the helical thread 17 of the drive member 14 under a force provided by the flexible arms 13 creates an audible and tactile feedback to the user to indicate that the dose has been set. Additionally, visual feedback regarding dose setting may be indicated by an optional graphical status indicator, provided on the drive member 14, which can be viewed through an optional window aperture in the main housing part 3.

When the dose has been set, the user may then dispense this dose by depressing the dispensing face 19 of the actuator 16. By this action the drive member 14 is moved axially in the distal direction relative to the main housing part 3. As the second thread 12 of the piston rod 10 is positively engaged with the helical thread 17 of the drive member 14 the piston rod 10 is caused to rotate with respect to the internal housing 7 by the axial movement of the drive member 14 in the distal direction. As the piston rod 10 rotates, the first thread 9 of the piston rod 10 rotates within the threaded circular opening 8 of the internal housing 7 causing the piston rod 10 to move axially in the distal direction with respect to the internal housing 7.

The distal axial movement of the piston rod 10 causes the pressure foot 11 to bear against the piston 5 of the cartridge 4 causing a dose of medicament to be dispensed through an attached needle.

The distal travel of the drive member 14 is limited by the guide slots (not shown) of the internal housing 7. The drive member 14 is provided with a detent means (not shown) that is designed to interact with the pawl means (not shown) of the internal housing 7.

Audible and tactile feedback to indicate that the dose has been dispensed is provided by the interaction of the detent of the drive member 14 with the pawl means of the internal housing 7. Additionally, visual feedback regarding dose dispensing may be indicated by an optional graphical status indicator, provided on the drive member 14, which can be viewed through an optional window aperture in the main housing part 3.

Further doses may be delivered as required up to a pre-determined maximum number of doses.

Figure 2:
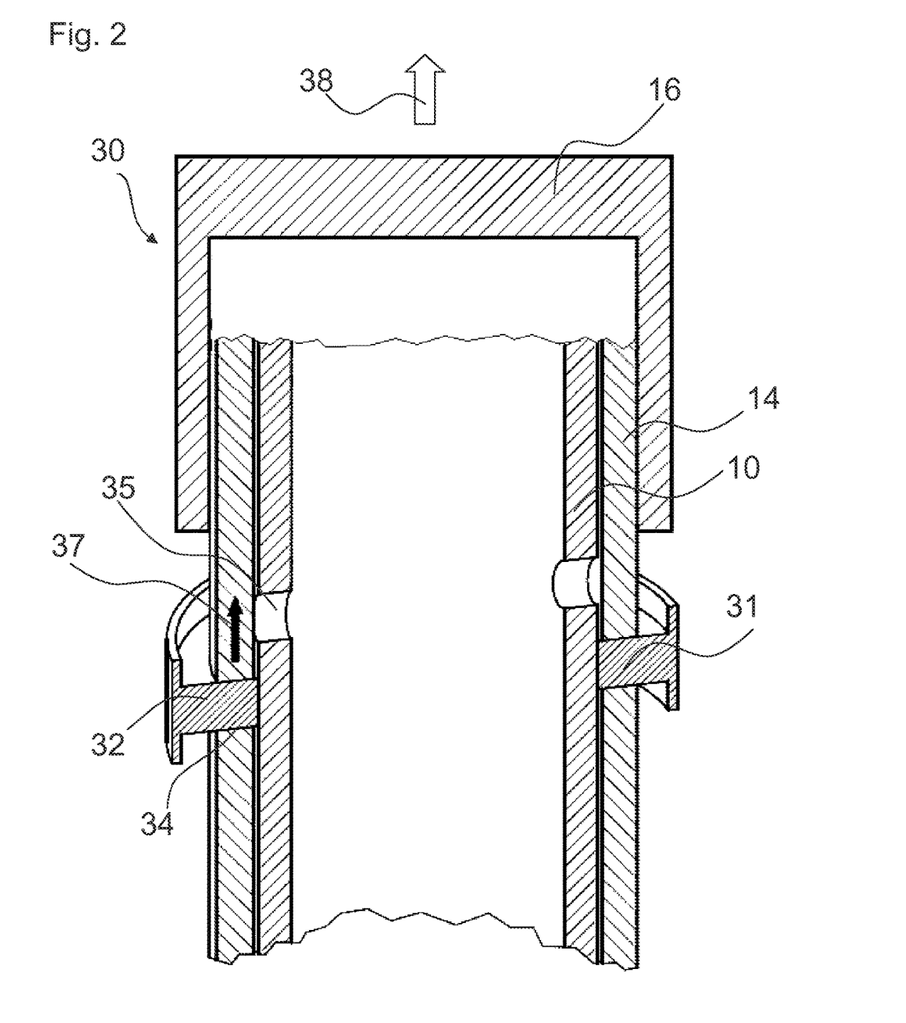
FIG. 2 shows an assembly for a drug delivery device.
Figure 3:
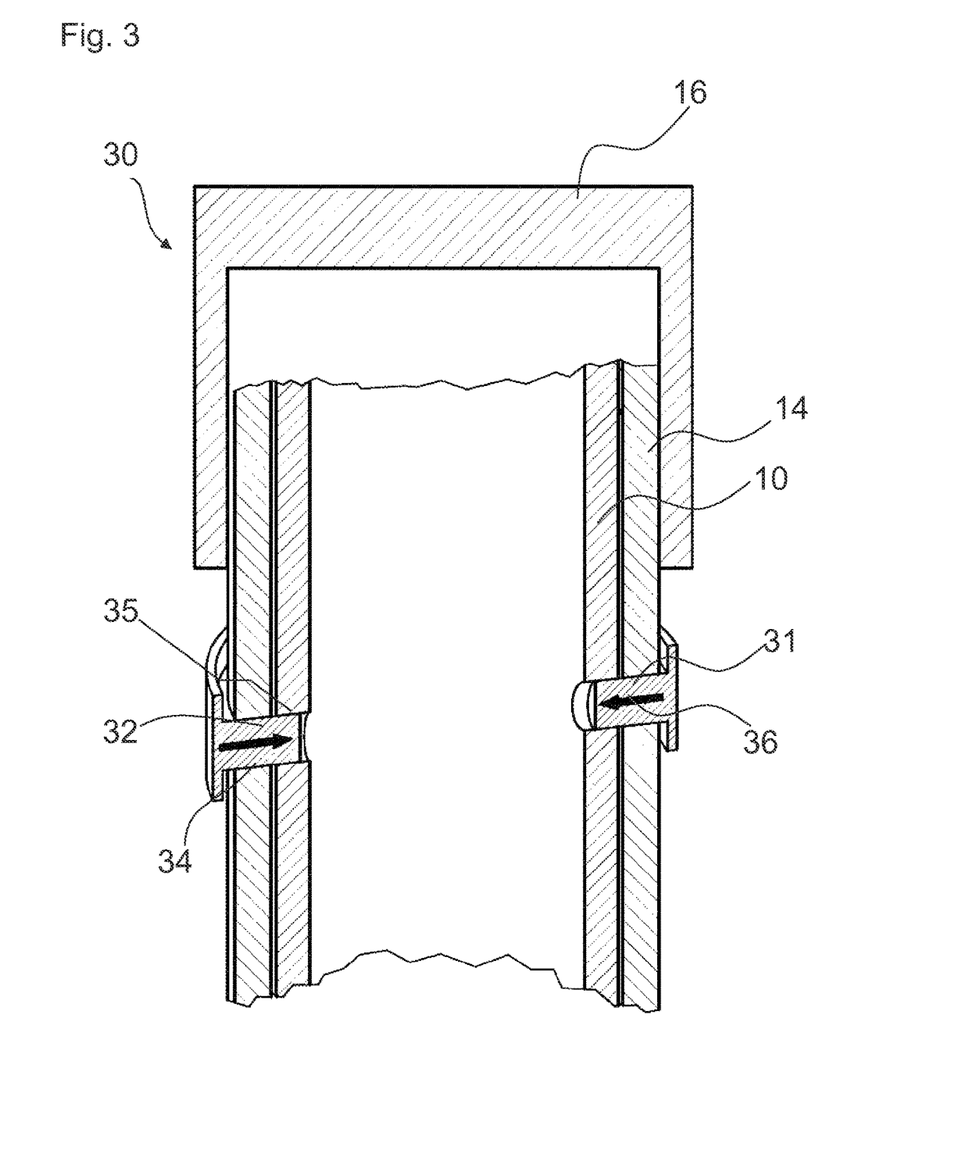
FIG. 3 shows the assembly of FIG. 1 in a different state.

FIG. 2 shows an assembly 30 for a drug delivery device, for example for a drug delivery device 1 as shown in FIG. 1. However, the assembly may also be used in an alternative drug delivery device. For example, the assembly may also be used in a variable dose device. The assembly 30 comprises a piston rod 10 and a snap feature 31. The piston rod 10 is configured as a lead screw. Furthermore, the assembly 30 comprises an actuator 16. The actuator 16 is configured as a button. The assembly 30 further comprises a drive member 14. The drive member 14 is configured as a drive sleeve. The actuator 16 may be fixedly coupled to the drive member 14, in particular to a proximal end of the drive member 14. In FIGS. 2 and 3, the drive member 14 and the piston rod 10 are plotted cropped at both ends, since in reality, the drive member and the piston rod farther extend in an axial direction. The actuator 16 is schematically attached to one cropped end of the drive member 14, in particular to the proximal cropped end of the drive member 14. In reality, the actuator is attached to the proximal end of the drive member 14, as shown in FIG. 1. However, the dimensions of FIGS. 2 and 3 may not be true to original, they only serve to exemplify the function of the assembly 30.

In FIG. 2, the assembly 30 is shown in a state before the assembly 30 is locked by the snap feature 31. In this state, the snap feature 31 may be preloaded due to the presence of the piston rod 10. In particular, the snap feature 31 may be deflected in a radial outward direction.

The actuator 16 is configured to be operated in order to dispense a dose of medication. In particular, the actuator 16 may be pushed in a distal direction in order to dispense a dose. Thereby, the drive member 14 may also be moved in a distal direction during the dispensing of a dose. In order to set a dose, the actuator 16 may be moved in a proximal direction, as indicated by arrow 38. For example, the actuator 16, and thereby the drive member 14, may perform an axial and non-rotational movement in a proximal direction. Alternatively, the actuator 16 and the drive member 14 may perform a combined axial and rotational movement in a proximal direction. Alternatively, the actuator 16 and the drive member 14 may perform a purely rotational movement. The drive member 14 is configured to drive the piston rod 10 in a distal direction in order to dispense a dose.

The assembly may be configured for use in a drug delivery device which may be a variable dose device such that a user can select the size of a dose. Alternatively, the assembly may be configured for use in a drug delivery device which may be a fixed dose device. The drug delivery device may be configured for multiple dose applications.

The snap feature 31 comprises the shape of a ring. The snap feature 31 may be a resilient member. In one embodiment, a segment of the ring may be cut out in order to increase the flexibility of the ring. Alternatively, the ring may be closed. The snap feature is arranged concentrically around the drive member 14 and concentrically around the piston rod 10. The snap feature 31 is permanently engaged with the drive member 14. In particular, the snap feature 31 is rotationally and axially fixed with respect to the drive member 14.

The drive member 14 comprises at least one, in particular two recesses 34, wherein the snap feature 31 is engaged with the recesses 34. In particular, the snap feature 31 comprises protrusions 32, which are permanently engaged with the recesses 34. The recesses 34 are configured as holes, which extend through the drive member 14. In particular, the holes extend in a radial direction with respect to a main axis of the device. The recesses 34 are oppositely arranged.

The snap feature 31 may be configured to lock the assembly 30 of the drug delivery device such that the setting or the dispensing of a dose may be inhibited after a last dose of medication has been delivered from the drug delivery device.

The snap feature 31 may engage with the piston rod 10 after a setting movement of the drive member 14. In particular, the snap feature 31 may be configured to lock the drive member 14 and the piston rod 10 with respect to each other such that no relative movement is possible between the drive member 14 and the piston rod 10. In particular, the snap feature 31 may be configured to engage with the piston rod 10 when the piston rod 10 and the drive member 14 are in a predetermined position with respect to each other.

The piston rod 10 comprises at least one, in particular two recesses 35, wherein the protrusions 32 of the snap feature 31 may engage with the recesses 35 of the piston rod 10 when the piston rod 10 and the drive member 14 are in a predetermined position with respect to each other. In particular, the snap feature 31 may engage with the piston rod 10 when the recesses 35 of the piston rod 10 are aligned to the recesses 34 of the drive member. In particular, the snap feature 31 may snap into the recesses 35 of the piston rod 10.

FIG. 3 shows the assembly 30 in a state where the snap feature 31 locks the assembly 30. In particular, when the drive member 14 and the piston rod 10 are in a predetermined position with respect to each other, the recesses 35 of the piston rod and the recesses 34 of the drive member 14 are aligned with respect to each other. In this position, the snap feature 31 may relax. In particular, the snap feature may deflect in a radial inward direction. In particular, the protrusions 32 of the snap feature 31 are engaged with the recesses 35 of the piston rod 10. Thereby, a relative movement between the drive member 14 and the piston rod 10 is inhibited.

According to one embodiment, the snap feature 31 may be configured to allow a last setting movement of the actuator 16 after a last dose has been delivered, but to inhibit a subsequent dispense movement. According to a further embodiment, the snap feature 31 is configured to inhibit a setting movement of the actuator 16 after a last dose has been delivered.

According to one exemplary embodiment, the assembly 30 may be used in a device wherein the drive member 14 may be moved along the piston rod 10 in a proximal direction during the setting of a dose, as indicated by arrow 37 in FIG. 2. Such a device is shown in FIG. 1. The drive member 14 may be configured to perform an axial, non-rotational movement. In particular, the drive member 14 may be rotationally fixed with respect to a housing (not shown) of the assembly 30. The piston rod 10 may be axially and rotationally fixed during the setting of a dose. During the dispensing of a dose, the piston rod 10 may be moved in a distal direction by the drive member 14 when a user operates the actuator 16. In particular, the piston rod 10 may perform a combined axial and rotational movement during the dispensing of a dose. A fixed dose device is described for example in document WO 2008/058665 A1.

When the device is empty, a last setting movement of the drive member 14 may be allowed. When the drive member 14 is moved in a proximal direction with respect to the piston rod 10, the recesses 34 of the drive member 14 may come to lie over the recess 35 of the piston rod 10. In this state, the snap feature 31 may engage with the piston rod 10, as indicated by the arrows 36 in FIG. 3. Thereby, the piston rod 10 and the drive member 14 are locked with respect to each other.

When a user tries to operate the actuator 16 after a last setting movement of the drive member 14, the piston rod 10 tries to rotate with respect to the drive member 14. Yet, such a rotational movement of the piston rod 10 is inhibited, since the piston rod 10 and the drive member 14 are locked with respect to each other. Consequently, the actuator 16 may not be operated by a user, and a dispense movement of the drive member 14 and the piston rod 10 is inhibited. Thereby, a user may recognize that the device is empty. Furthermore, the actuator 16 may permanently protrude from the device, which gives an additional, visible indication to a user that the device is empty.

According to a further exemplary embodiment, the drive member 14 may be rotated along the piston rod 10 in a proximal direction during the setting of a dose, while the piston rod 10 may be fixed with respect to a housing (not shown) of the drug delivery device. In particular, the piston rod 10 and the drive member 14 may be in a threaded engagement. When a dose is set which is equal to an amount of medication left in a cartridge of the device, the snap feature 31 may engage with the piston rod 10 and thereby lock the piston rod 10 and the drive member 14 with respect to each other. FIG. 3 shows the assembly 30 with the snap feature 31 being in engagement with the piston rod 10.

Subsequently, the actuator 16 may be pushed in a distal direction by a user. Thereby, the drive member 14 and the piston rod 10 may be both moved in a distal direction. In particular, the drive member 14 and the piston rod 10 perform an axial, non-rotational movement during the dispensing of a dose. Thereby, a last dose may be delivered from the drug delivery device.

A subsequent setting of a dose is inhibited by means of the snap feature 31, since the drive member 14 cannot be rotated with respect to the piston rod 10 anymore. Thereby, a user may recognize that the device is empty.

The invention claimed is:

1. An assembly for a drug delivery device, the assembly comprising:
   an actuator which is user-operable and has at least one surface arranged to be touched by a user for setting or delivering a dose, wherein the actuator is configured to perform a setting movement by moving proximally in order to set the dose and to perform a dispense movement by moving distally in order to dispense the dose;
   a piston rod configured to be moved in a distal direction in order to dispense the dose;
   a drive sleeve configured to drive the piston rod towards a distal end of the drug delivery device to deliver the dose, wherein the actuator is fixedly coupled axially and rotationally to the drive sleeve so as to inhibit relative axial and rotational movement between the actuator and the drive sleeve; and
   a snap feature configured to snap into engagement with the piston rod when the actuator is performing the setting movement,
   wherein the snap feature is configured to inhibit a dispense movement of the actuator when a maximum amount of medication has been delivered.

2. An assembly for a drug delivery device, the assembly comprising:
   an actuator fixedly coupled axially and rotationally to a drive member having an outer surface, wherein the actuator and the drive member are moved together proximally relative to a piston rod to perform a setting movement in order to set a dose so as to inhibit relative axial and rotational movement between the actuator and the drive member,
   wherein the actuator and the drive member are moved distally to perform a dispense movement in order to dispense the dose, and the piston rod is moved in a distal direction in order to dispense a dose; and
   a snap feature axially fixed to the drive member in a first preloaded state, wherein a portion of the snap feature extends radially through the drive member and contacts the piston rod so that the snap feature is deflected radially outward, and the snap feature is configured to snap into engagement with the piston rod when the snap feature moves from the first preloaded state to a relaxed state as the drive member moves proximally during the setting movement,
   wherein, when the snap feature is in the relaxed state, the snap feature inhibits at least one of a dispense movement of the actuator and a setting movement of the actuator when the maximum amount of medication has been delivered.

3. The assembly according to claim 2, wherein the snap feature is configured to inhibit the dispense movement of the actuator after a last setting movement when a maximum amount of medication has been delivered.

4. The assembly according to claim 3, wherein the snap feature is configured to snap into engagement with the piston rod after the last setting movement of the actuator.

5. The assembly according to claim 2, wherein the snap feature is configured as a resilient member.

6. The assembly according to claim 2, wherein the snap feature is ring shaped.

7. The assembly according to claim 2, wherein the piston rod comprises at least one recess, and wherein the snap feature is configured to engage with the recess.

8. The assembly according to claim 2, wherein the snap feature is arranged concentrically with respect to the piston rod.

9. The assembly according to claim 2, wherein the drive member comprises at least one recess, and wherein the snap feature comprises at least one protrusion which is permanently engaged with the recess of the drive member.

10. The assembly according to claim 9, wherein the piston rod comprises at least one recess, and wherein the snap feature is configured to engage with the at least one recess of the piston rod when the at least one recess of the piston rod and the at least one recess of the drive member are aligned with respect to each other.

11. The assembly according to claim 9, wherein the snap feature is rotationally and axially fixed with respect to the drive member.

12. The assembly according to claim 9, wherein the drive member and the piston rod are locked relative to each other when the snap feature is engaged with the piston rod.

13. The assembly according to claim 9, wherein the snap feature is arranged concentrically around the drive member.

14. A drug delivery device comprising the assembly according to claim 2.

* * * * *